_US006046237A_

United States Patent [19]
Berge et al.

[11] Patent Number: 6,046,237
[45] Date of Patent: Apr. 4, 2000

[54] NON-β-OXIDIZABLE FATTY ACID ANALOGUES, THEIR USES AS THERAPEUTIC ACTIVE MEDICAMENTS

[76] Inventors: Rolf Berge, Tjørnhaugen 50, N-5062 Bønes; Jon Songstad, Nystuveien 21, N-5019 Bergen, both of Norway

[21] Appl. No.: 08/981,956
[22] PCT Filed: Oct. 25, 1995
[86] PCT No.: PCT/NO95/00195
   § 371 Date: Jan. 20, 1998
   § 102(e) Date: Jan. 20, 1998
[87] PCT Pub. No.: WO97/03663
   PCT Pub. Date: Feb. 6, 1997

[30] Foreign Application Priority Data

Jul. 14, 1995 [NO] Norway ..................... 952796

[51] Int. Cl.[7] ..................... A01N 37/02
[52] U.S. Cl. ............ 514/546; 514/550; 514/557
[58] Field of Search ............... 514/550, 546, 514/557; 562/899

[56] References Cited

U.S. PATENT DOCUMENTS 5,093,365  3/1992  Berge et al. ............... 514/550

FOREIGN PATENT DOCUMENTS 0345038  12/1989  European Pat. Off. .

OTHER PUBLICATIONS

Sadak, S. A.; Basmadjian, G.P.J. Labelled Compd. Radiopharm. 20(4), 487–494, 1983.

Schwarz, K.; Fredga, A. Chem Abstract 80:10264, 1974.

STN International, File CA, Chemical Abstracts, vol. 124, No. 9, Feb 26, 1996, (Columbus Ohio, US), Froeyland, Livar et al: "Tetradecylthioacetic acid incorporated into very low density lipoprotein: changes in the fatty acid composition and reduced plasma lipids in cholesterol–fed hamsters", Abstract No. 115981, and J. Lipid Res. (1995), 36 (12), 2529–40.

*Primary Examiner*—Gary Geist
*Assistant Examiner*—Robert W. Deemie
*Attorney, Agent, or Firm*—McAulay Nissen Goldberg Kiel & Hand, LLP

[57] ABSTRACT

There are disclosed compounds of the general formula (I): alkyl-X-$CH_2$COOR wherein alkyl represents a saturated or unsaturated hydrocarbon of 8–26 carbon atoms, X represents a sulfur atom or a selenium atom and R is hydrogen or $C_1$–$C_4$ alkyl. Said compounds are used for the manufacturing of medicaments for the treatment of hyperlipidemic conditions, (arteriosclerotic disease), coronary artery disease and for reducing the concentration of lipids in blood of mammals, for inhibiting oxidative modification of LDL, and for reducing proliferation of cancer cells. Methods for preparing the compounds are also disclosed.

15 Claims, No Drawings

NON-β-OXIDIZABLE FATTY ACID ANALOGUES, THEIR USES AS THERAPEUTIC ACTIVE MEDICAMENTS

This invention relates to the use of certain non-β-oxidizable fatty acid analogues for the manufacture of medicaments for the treatment of hyperlipidermic conditions, such as for reducing the concentration of cholesterol and triglycerides, and for inhibition of the oxidative modification of low density lipoprotein (LDL) in the blood of mammals. These medicaments also have a preventive effect on growth of tumour cells and may therefore be used in treatment of various terms of cancer diseases. The invention also relates to a method for preparing a medicament based on the mentioned fatty acid analogues, and also relates to a new compound having all of the above given favourable therapeutical effects.

Excess of cholesterol and triglycerides in blood has been shown to accelerate the development of ateriosclerosis and is a risk factor for myocardial infarction. Accordingly, a reduction of excess of lipids in blood by diets or drugs is used as a preventative measure in people at risk due to high levels of cholesterol and triglycerides and high platelet activation.

In this connection reference is made to European Patent Specification No. 345.038 (NORSK HYDRO A.S., priority of GB-8813012 of Jun. 2, 1988) which discloses the use of non-β-oxidizable fatty acid analogues of the general formula (I):

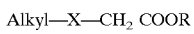

Alkyl—X—CH$_2$ COOR wherein alkyl represents a saturated or unsaturated hydrocarbon group of from 8–22 carbon atoms, X represents O, S, SO, and SO$_2$, and R represents hydrogen or C$_1$–C$_4$ alkyl, for the manufacture of a medicament for the treatment of hyperlipaemic conditions and for reducing the concentration of cholesterol and triglycerides in the blood of mammals. The EP-specification also discloses the preparation of compounds of the actual non-β-oxidizable fatty acid analogues wherein the substituent X represents O, S, SO, SO$_2$, respectively. The EP-specification reports that the compounds in question exhibit favourable hypolipidemic effects in blood of mammals, such as rats, and possess low toxicity measured as increase in liver weight and increased peroxisomal β-oxidation. The patent concludes that the compounds in question are potentially useful as medicinal compounds. For further considerations we refer to the EP-specification.

It has now been found that the analogues of the above mentioned non-β-oxidizable fatty acid have broader area of applications as an ingredient in drugs than the ones reported in the European Patent Specification No. 0.345.038. Further, it has been found that analogues with other election for the substituent X in the compound of formula (I), exhibit, as will be evident from the below specification, generally more potent pharmaceutical effects, also regarding the previously disclosed teaching of treatment of hyperlipidermic conditions for reducing the concentration of cholesterol and triglycerides. Current research suggests that prevention of atherosclerosis must take into consideration not just lowering plasma cholesterol and triglycerides, but also decreasing the susceptibility of LDL to oxidative damage. Oxidatively modified LDL—but not native LDL—has a number of characteristic properties that may initiate formation of foam cells and promote the development of fatty streaks, the earliest lesions in atherosclerosis. It could therefore be expected that preventing LDL modification could alternate foam cell formation and the development of plaques. It is well known that natural long-chain fatty acids, particularly polyunsaturated fatty acids of the main origin, are effective in lowering plasma triglyceride but not cholesterol levels in man. Moreover, as a lipid radical-propagated peroxidation chain reaction, in which the polyunsaturated fatty acids contained in the LDL are rapidly oxidized to lipid hydroperoxides, high supplementation of main based diets rich in ω-3-fatty acids may rather increase LDL oxidation.

The antiatherogenic properties of probucol are supposed to be related to its antioxidant effect rather than to its relatively weak hypocholesterolemic potency.

New strategies have been developed to search for compounds that are likely to protect against radical damage in order to prevent modification of LDL and at the same time be an effective lipid-lowering drug. Considering that polyunsaturated fatty acids are metabolized slowly, we postulated that simple fatty acid analogues blocked for β-oxidation with a reducing agent or atom might result in a very potent compound being able to inhibit LDL oxidative modification and to lower blood lipids.

In feeding experiments with such fatty acid analogues the results show that they lower the blood concentration of cholesterol and triglycerides and inhibit LDL oxidative modification, without any overt toxic effect.

These fatty acids analogues are to the best of our knowledge the simplest lipid and antioxidant compounds found so far.

Considering that there is substantial evidence that polyunsaturated fatty acids from the n-3 family (ω-3 fatty acids) which are metabolized relatively slowly and reduce proliferation of cancer cells, we postulated that simple non-β-oxidizable fatty acid analogues might have similar effects. Results of in vitro experiments with such fatty acid analogues show that they reduce the rate of proliferation and effect differentiation of cancer cells much more effectively than pure ω-3 fatty acids do.

Thus, the present invention provides fatty acid analogues with the ability a) to lower concentration of cholesterol and triglycerides in the blood b) to inhibit LDL oxidative modification, and c) to reduce the rate of proliferation of cancer cells. The fatty acid analogues of the present invention provides improved effect relative to ω-3 fatty acids and without undesirable side effects.

More particularly, the present invention is the use of non-β-oxidizable fatty acid analogues of the general formula (I) Alkyl-X-CH$_2$ COOR wherein alkyl represents a saturated or unsaturated hydrocarbon group of from 8–26 carbon atoms, X represents a selenium atom, and R is hydrogen or C$_1$–C$_4$ alkyl, for the manufacture of a medicament for a) the treatment of hyperlipidemic and antherogenic conditions, such as for reducing the concentration of cholesterol and triglycerides in the blood of mammals, b) to inhibit the oxidative of low density lipoprotein (LDL), and c) to reduce the growth of cancer cells.

Preferably the alkyl group is the tetradecyl group. In another aspect the compound of formula (I) is tetradecylselenoacetic acid.

In accordance with another aspect, the invention relates to a process for the manufacture of a medicament for a) treatment of hyperlipidermic conditions and for reducing the concentration of cholesterol and triglycerides in the blood of mammals, b) to inhibit the oxidative modification of low density lipoprotein (LDL), and c) to reduce the growth of cancer cells, comprising incorporating with a pharmaceutical acceptable carrier or diluent, a non-β-oxidizable fatty acid analogue of the general formula (I):

Alkyl—X—CH$_2$ COOR wherein Alkyl represents a saturated or unsaturated hydrocarbon group of from 8–22 carbon atoms, X represents a selenium atom and R is hydrogen of C$_1$–C$_4$ alkyl. Preferably the alkyl group is the tetradecyl group. In another aspect the compound of formula (I) is tetradecylselenoacetic acid.

In accordance with an another further aspect the present invention comprises a fatty acid analogue of the general formula (I): Alkyl—X—CH$_2$ COOR wherein Alkyl represents a saturated or unsaturated hydrocarbon group of from 8–22 carbon atoms, X represents a selenium atom and R is hydrogen or C$_1$–C$_4$ alkyl. Preferably the alkyl group is the tetradecyl group. In another aspect the compound of formula (I) is tetradecylselenoacetic acid.

In accordance with an another aspect of the invention, use is made of non-β-oxidizable fatty acid analogues compounds of the abovementioned formula (I), with the exception of the substituent X being a sulfur atom, in order to inhibit the oxidative modification of low density lipoprotein (LDL), and to reduce the growth of cancer cells. Preferably the alkyl group is the tetradecyl group. In another aspect the compound of formula (I) is tetradecylsthioacetic acid.

In accordance with yet a further aspect of the invention relates to a process for the manufacture of a medicament to inhibit the oxidative modification of low density lipoprotein (LDL), and to reduce the growth of cancer cells, comprising incorporating with a pharmaceutical acceptable carrier or diluent, a non-β-oxidizable fatty acid analogue of the general formula (I): Alkyl—X—CH$_2$ COOR wherein Alkyl represents a saturated or unsaturated hydrocarbon group of from 8–22 carbon atoms, X represents a sulfur atom and R is hydrogen or C$_1$–C$_4$ alkyl. Preferably the alkyl group is the tetradecyl group. In another aspect the compound of formula (I) is tetradecylsthioacetic acid.

Thus, therapeutical active medicaments are manufactured by incorporating a compound in question with a pharmaceutical acceptable carrier or diluent.

The compounds used according to the present invention wherein the substituent X is a sulphur atom or selenium atom may be prepared according to the following general procedure:

X is a Sulfur Atom

The thio-substituted compound used according to the present invention may be prepared by the general procedure indicated below:

The preparation of a number of non-β-oxidizable fatty acid derivates of formula (I) above will now be given by way of illustration.

EXAMPLE 1

Synthesis of Tetradecylthioacetic acid CH$_3$—(CH$_2$)$_{13}$—S—CH$_2$—COOH. Compound I.

KOH, 20 g (0,3 equivalents), mercaptoacetic acid, 12 ml (0,14 equivalents), and tetradecyl bromide, 25 ml (0,09 equivalents), were added in that order to 200 ml methanol and the solution was stirred overnight in a nitrogen atmosphere. A white precipitate of potassium bromide was formed. To the reaction mixture concentrated HCl (30 ml) dissolved in water (400 ml) was then added. Tetradecylthioacetic acid started to precipitate immediately and the solution was left overnight at room temperature to complete this process. The product was then isolated by filtration and washed four times with water. After drying the product was crystallized once from diethyl ether and then twice from methanol. Tetradecylthioacetic acid appeared as white flakes with a melting point of 68° C.

Yield: 23 g=75% as based on the amount of tetradecyl bromide used. $^1$H-NMR (in CDCl$_3$=: δ0,84–0,91 (t,3H, CH$_3$), 1,25–1,45(m,22H, 11 CH$_2$) 1,60–1,73 (p,2H,—CH$_2$CH$_2$S—), 2,62–2,66 (t,4H, —CH$_2$S—), 3,24 (s,2H,S—CH$_2$COOH), 10,6 (s,1H, COOH).

X is a Selenium Atom

The seleno-substituted compound used according to the present invention may be prepared by the following general procedure:

1. Alkyl—Hal+KSeCN→Alkyl—SeCN
2. Alkyl—SeCN+BH$_4$$^-$→Alkyl—Se
3. Alkyl—Se$^-$+O$_2$→Alkyl—Se—Se—Alkyl This compound is purified by careful crystallization from ethanol or methanol.

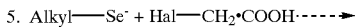

Alkyl—Se—CG$_2$—COOH

The final compound, f.ex. when Alkyl is tetradecyl, CH$_3$(CH$_2$)$_{13}$—Se—CH$_2$—COOH, can be purified by crystallization from diethyl ether/hexane. This product may be fully characterized by NMR, IR and molecular weight determination.

In the present case, the selenium compound tetradecylselenoacetic acid of formula CH$_3$(CH$_2$)$_{13}$—Se—CH$_2$—COOH (Compound II) was prepared.

EXAMPLE 2

Synthesis of tetradecylselenoacetic acid: CH$_3$—(CH$_2$)$_{13}$—Se—CH$_2$—COOH. Compound II.

1. Synthesis of ditetradecyl diselenide: CH$_3$(CH$_2$)$_{13}$—Se—Se—(CH$_2$)$_{13}$CH$_3$.

Black selenium, 3,54 g (0,045 mol), was suspended in 150 ml 1:1 mixture of tetrahydrofuran (THF) and water in an argon atmosphere. Sodium borohydride (NaBH$_4$), 3,93 g (0,10 mol), in 60 ml of argon-flushed THF:H$_2$O (1:1) was added dropwise to the suspension (careful, exothermic). A reddish brown colour was initially formed but gradually disappeared. To this solution was added selenium, 3,54 g (0,045 mol), suspended in 150 ml THF:H$_2$O (1:1). A reddish-brown solution was formed. The reaction mixture was stirred for 15 min and finally heated for about 10 min to complete the dissolution of selenium. Tetradecyl bromide, 24,9 g (0,09 mol), in THF (50 ml) was then added to the solution. During one hour with gentle heating the solution turned yellow indicating the reaction to be completed. The reaction mixture was treated with chloroform and the organic layer was dried over anhydrous magnesium sulphate, filtered and evaporated to leave a yellow oil solidified upon cooling. Crystallization from diethyl ether gave yellow needles with a melting point of 43° C.

Yield: 20 g=80% as based on the amount of tetradecyl bromide used.

2. Synthesis of tetradecylselenoacetic acid: CH$_3$(CH$_2$)$_{13}$—Se—CH$_2$COOH. Compound II.

To the diselenide, 1,0 g (0,0018 mol), in 25 ml THF (freshly distilled from benzophenon and sodium) was added dripwise NaBH$_4$, 0,206 g (0,0054 mol), dissolved in 10 ml H₂O in an argon atmosphere. After the solution had been decolorized with bromoacetic acid 1,0 g (0,0072 mol), and triethylamine, 1,0 ml (0,0072 mol), in THF (25 ml) was added and the solution was stirred for 6 h at room temperature. Water (50 ml) was then added and the solution was treated with diethyl ether. The organic layer was discarded. The aqueous layer was acidified with HCl and extracted with diethyl ether. The ether layer was dried over anhydrous magnesium sulphate, filtered and was evaporated in vacuum leaving a white solid. Crystallizations, one from hexane (30 ml) and then from diethyl ether (30 ml), left white crystals of tetradecylselenoacetic acid with a melting point of 68° C. Yield: 0,80 g=66% as based on the amount of ditetradecyl diselenide used.

$^1$H-NMR (in CDCl$_3$): δ0,84–0,91 (t,3H,CH$_3$), 1,25–1,45 (m,22H, 11 CH$_2$), 1,62–1,73 (p, 2H, —C$\underline{H}_2$Se—), 2,8—3,06 (t,4H, —CH$_2$Se—), 3,15 (s,2H, —Se—C$\underline{H}_2$COOH), 10,6 (s1H, COOH).

The pharmaceutical effects of the compounds prepared as disclosed above according to the present invention will now be disclosed further in the following experiments which are presented in the tables. The compounds I and II prepared as disclosed above were used in the experiments.

Experiments

Lipid Lowering Effect

Male wistar rats, weighing 180–200 g at the start of the experiment, were housed individually in metal wire cages in a room maintained at 12 h light-dark cycles and a constant temperature of 20±3° C. The animals were acclimatized for one week under these conditions before the start of the experiments.

Compound I (tetradecylthioacetic acid), compound II (tetradecylselenoacetic acid) prepared in accordance with Examples 1 and 2, and eicosapentaenoic acid (EPA) were suspended in 0,5% (w/v) carboxymethyl cellulose (CMC). Six animals were used for each treatment and a 0,5% CMC solution was administered to rats as control. After administration of the test compound, rats were fasted for 12 hours and anesthetized with haloethan. Eicosapentaenoic acid and the fatty acid derivatives were administered by gastric intubation (gavage) once daily for 7 days. Blood samples were collected by cardiac puncture, and lipid concentrations in plasma were determined using an autoanalyzer. Results obtained with Se-tetradecylseleno-acetic acid (compound II), EPA and tetradecylthioacetic acid (compound I), are reported in Table 1.

TABLE 1

Effect of compound I, compound II and EPA - lipid lowering drug on plasma lipid levels in rats.

| Compound | Dose mg/day/kg body weight | Decreased Plasma lipids (% of control) triglycerides | cholesterol |
|---|---|---|---|
| Compound II (Se-tetradecyl-selenoacetic acid) | 15 | 25 | 20 |
| Eicosapenta-enoic acid | 1500 | 20 | 18 |
| Compound I (Tetradecylthio-acetic acid) | 150 | 45 | 30 |

Table 1 shows that tetradecylselenoacetic acid (Compound II) exhibits a good lipid lowering effect in blood of mammals, such as rats, and posesses low toxicity measured as increase in liver weight and increased peroxisomal β-oxidation (data not shown). It will appear that a 100 times greater dose of the lipid lowering drug eicosapentaenoic acid is necessary to obtain the same decreased plasma lipid results as obtained for compound II (tetradecylselenoacetic acid). Moreover, the substituted fatty acid compounds are much more effective than pure EPA and fish oil in lowering plasma lipids. Therefore they are potentially useful as medical compounds.

In another set of experiments hepatocytes from rats, not treated with the test compounds, were prepared. Cultured hepatocytes were incubated for 4 hours with [1-$^{14}$C] palmitic acid (200 μM) in the presence of L-carnitine (0,5 mM) and the different drugs (Table 2) and medium triglycerides (secreted) were extracted and dissolved in n-hexane and separated by thin-layer chromatography on silica plates developed in hexane-diethylether-glacial acetic acid with a ratio of 80:20:1. The bands were visualized by iodine vapor, cut into pieces and counted.

TABLE 2

Effect of tetradecylthioacetic acid (compound I), tetradecylselenoacetic acid (compound II), the EPA and oleic acid lipid lowering drugs (200 μM) on secretion of triglyceride-labeled [1-$^{14}$C] palmitic acid from hepatocytes incubated with [1-$^{14}$C] palmic acid (200 μM). Results are given as mean ± SD for values obtained from five independent experiments.

| Compound | Secretion of [1-$^{14}$C] palmitic acid labeled triglycerides (nmol/protein/4 hours) |
|---|---|
| Compound II tetradecyl-selenoacetic acid | 14,4 +/− 6,7** |
| Eicosapenta-enoic acid | 24,4 +/− 10,2* |
| Compound I Tetradecylthio-acetic acid | 18,4 +/− 5,9** |
| Oleic acid | 34,7 +/− 5,96 |

*p < 0,05 compared to oleic acid (control).
**p < 0,01 compared control.

Table 2 shows that hepatocytes of rats grown with tetradecylselenoacetic acid and tetradecylthioacetic acid caused a statistically significant lower secretion of palmitic-acid-labeled triglycerides that did oleic acid.

Antioxidant Effect

EXAMPLE 3

Male wistar rats, weighing 180–200 g at the start of the experiment, were housed individually in metal wire cages in a room maintained at 12 h light-dark cycles and a constant temperature of 20±3° C. The animals were acclimatized for one week under these conditions before the start of the experiments.

Compounds I and II according to the invention, and other fatty acid derivatives, were suspended in 0,5% (w/v) carboxymethyl cellulose (CMC). The fatty acid derivatives were administered by gastric intubation (gavage) once daily for different days. The antioxidant effect as a function of the dose administered was examined.

Six animals were used for each treatment and a 0,5% CMC solution was administered to rats as control. After administration of the test compound, rats were fasted for 12 hours and anesthetized with haloethan. Blood samples were collected by cardiac puncture and LDL preparations were prepared by ultracentrifugation.

In other set of experiments where the acid derivatives were administered at a dose of 250 mg/day/kg body weight, the antioxidant effects of different fatty acid derivatives were compared with that of control. In this experiment the dosing lasted for 7 days. In all these in vivo experiments, adding tetradecylselenoacetic acid (compound II) and tetradecylthioacetic acid (compound I) to plasma as an antioxidant to prevent modification of LDL, in vitro, dramatically increase the lag time (data not shown). Thus the results indicate that compounds I and II achieves a modification of LDL as the lag time increased. Therefore they are potentially useful as medical antioxidants.

EXAMPLE 4.

Low-density lipoproteins (LDL) were prepared from fresh normal human plasma by sequential ultracentrifugation. LDL were taken as the 1.021 to 1.063 density fraction, dialysed and the oxidation was initiated by addition of $CuSO_4$. The kinetics of LDL oxidation were determined by monitoring the change in absorbence at 234 nm (nano meter) (conjugated dienes). The change in absorbence at 234 nm vs time could be divided into three consecutive phases: lag, propagation and decomposition where the lag time is defined as the interval (minutes) between the intercept of the linear least-square slope of the curve with the initial-absorbence axis.

Table 3 shows that addition of tetradecylselenoacetic acid (compound II) and tetradecylthioacetic acid (compound I) increased the lag time in a dose-dependent manner of $Cu^{2+}$-treated LDL. Tetradecylselenoacetic acid (compound II) was much more potent that tetradecylthioacetic acid in the same experimental conditions. Addition of palmitic acid analogues, oxidized 3-thia fatty acid and 3-oxygen substituted fatty acid analogues did not changed the modification of LDL (Table 3).

TABLE 3

Effect of tetradecylselenoacetic acid (compound II) and tetradecylthioacetic acid (compound I) on modification of LDL from human plasma.

| Compound added/concentration | lag Time (min) |
| --- | --- |
| No addition (control) | 44,1 ± 0,3 |
| Palmitic acid | |
| 5 μM | 48,2 ± 4,8 |
| 10 μM | 51,6 ± 4,8 |
| 20 μM | 50,6 ± 9,6 |
| Tetradecylthioacetic acid (compound I): | |
| 5 μM | 58,1 ± 9,6 |
| 10 μM | 78,5 ± 11,6 |
| 20 μM | 111,3 ± 23,1 |
| Tetradecylselenoacetic acid (Compound II): | |
| 1 μM | 74,2 ± 6,8* |
| 2 μM | 86,9 ± 7,6* |
| 3 μM | 152,3 ± 11,5* |
| Tetradecylsulfonylacetic acid: | |
| 20 μM | 48,2 ± 7,1 |
| Tetradecyloxyacetic acid | |
| 20 μM | 51,6 ± 6,2 |

*p < 0,05 compared to control

For such purposes, the compounds of the present invention can be administered orally or parenterally in a conventional dosage or parenterally in a convential dosage form such as tablets, capsules, powders, emulsions and solutions prepared according to conventional pharmaceutical practices.

Reduced Proliferation of Cancer Cell

The effect of tetradecylselenoacetic acid (compound II) and tetradecylthioacetic acid (compound I) on many different cell lines, as specified in the left column of the following table 4, were studied.

Generally, the cells were grown in a humidified (95%) atmosphere of 5% $CO_2$ and 95% $O_2$ (air) maintained at 37° C. All experiments were carried out using cell culture plates initially, the cells were plated, i.e. allowed to attach to the bottom, by incubating with plating medium CDulbeccos minimum essential medium.

Each of the test compounds I and II was incubated to each of isolated cell populations in a concentration of 100 μm. Palmitic acid in a concentration of 100 μM was also added to a population as a control sample. The cell number in all samples was counted six days after the start time of the incubation by using standard techniques.

For the cells of mamma cancer (MCF-7) also Eicosapentaenoic acid and Docahexaenoic acid were tested similarly in concentrations of 100 μM each.

The results are presented in table 4 as the cell number in each sample following six days of incubation in procentage of the control, wherein the palmitic acid (the control) is given as 100%.

TABLE 4

Effect of tetradecylselenoacetic acid (compound II), tetradecylthioacetic acid (compound I), and unsaturated fatty acids on cancer cell growth.

| Cells | Compounds | Cell number following six days of incubation (% of control) |
| --- | --- | --- |
| Brain glioma rat | | |
| BT4C | Palmitic acid | 100 |
| | compound II | 60 |
| | Tetradecylthioacetic acid | 65 |
| BT4CN | Palmitic acid | 98 |
| | compound II | 70 |
| | Tetradecylthioacetic acid | 68 |
| Brain glioma, human | | |
| D-37MG | Palmitic acid | 100 |
| | compound II | 40 |
| | Tetradecylthioacetic acid | 35 |
| D-54MG | Palmitic acid | 100 |
| | compound II | 55 |
| | Tetradecylthioacetic acid | 50 |
| GaMG | Palmitic acid | 100 |
| | compound II | 60 |
| | Tetradecylthioacetic acid | 55 |
| Leucemic, human | | |
| HL-60 | Palmitic acid | 100 |
| | compound II | 40 |
| | Tetradecylthioacetic acid | 35 |
| KGla | Palmitic acid | 100 |
| | compound II | 60 |
| | Tetradecylthioacetic acid | 65 |
| Mamma cancer | | |
| MCF-7 | Palmitic acid | 100 |
| | compound II | 60 |
| | Tetradecylthioacetic acid | 55 |
| | Eicosapentaenoic acid | 76 |
| | Docahexaenoic acid | 98 |

The added concentration of the different fatty acids was 100 μM.

For all cell lines each of the compounds I and II exhibits a significant lower value for the count of the cell numbers than do the control compound of palmitic acid. For most of the tested compounds a reduction of proliferation of up to 40% or more was obtained.

As also will appear from table 4, compounds I and II inhibit the proliferation of the cell line of mamma cancer MCF-7 to a greater extent than eicosapentaenoic acid and docahexenoic acid.

The effect of various doses of compound I, compound II, palmitic acid, eicosapentaenoic acid and docahexenoic acid, on the cell number was measured by adding each of said compounds at different concentrations, i.e. at concentrations of 10, 20, 50, 100, and 150 μM, to isolated cell cultures of MCF-7 breast cancer. The number of cancer cells were counted 6 days following incubation by using standard techniques. The results are shown in the following table 5.

TABLE 5

Effect of tetradecylselenoacetic acid and tetradecylthioacetic acid at different doses on MCF-7 breast cancer cell growth.

| Compound | Cell numbers (x10$^3$) in the presence of fatty acids at different concentrations (μM) | | | | | |
|---|---|---|---|---|---|---|
| | 0 | 10 | 20 | 50 | 100 | 150 |
| Palmitic acid | 746 | 658 | 715 | 642 | 710 | 730 |
| Tetradecylseleno-acetic acid | 737 | 689 | 590 | 520 | 440 | 420 |
| Tetradecylthio-acetic acid | 740 | 637 | 570 | 480 | 410 | 400 |
| Eicosapentaenoic acid | 630 | 665 | 605 | 520 | 480 | 420 |
| Docahexaenoic acid | 583 | 615 | 626 | 624 | 599 | 610 |

Table 5 shows that the compounds to various extents effected a reduction in cell number, i.e. a cancer cell prolifation. However, the proliferation was significantly greater for compounds I and II than for the other compounds in the test.

Tables 4 and 5 show that compounds I and II achieved a significant reduction in the rate of proliferation of cancer cells. Therefore the compounds are potentially useful as medicinal compounds.

The compounds used according to the present invention may be administered to patients suffering from any type of dyslipidaemia except type I. As antioxidants they can be used for various cardiovascular diseases. Regarding the reduced proliferation of cancer cells, they may be administered to patients suffering from any type of cancer. Alternatively by dietary they may prevent disease as atherosclerosis and tumor formation.

The dosage range for the compounds according to the present application is contemplated to be from 5 to 100 mg/day for the average adult patient. Of course, the actual dose necessary will depend on the patient's condition and will have to be determined by the attending physician from case-to-case.

For oral pharmaceutical compositions such carrier material as, for example, water, gelatine, gums, lactose, starches, magnesium-stearate, talc, oils, polyalkylene glycol, petroleum jelly and the like may be used. Such pharmaceutical preparation may be in unit dosage form and may additionally contain other therapeutically valuable substances or conventional pharmaceutical adjuvants such as preservatives, stabilizing agents, emulsifiers, buffers and the like. The pharmaceutical preparations may be in conventional solid dosage forms such as tablets, capsules, dragees and the like, in conventional liquid forms such as solutions, suspension, emulsions and the like, and other conventional dosage forms such as dry ampulles, suppositories and the like.

For parenteral administration the compounds according to the present invention may be administered as solutions, suspensions or emulsions using conventional pharmaceutical carrier materials such as for example water for injection, oils, polyalkylene glycols and the like. These pharmaceutical preparations may further include conventional pharmaceutical adjuvants, such as preservatives, stabilizing agents, wetting agents, emulsiers, salts for the adjustment of the osmotic pressure, buffers and the like. The preparations may also contain other therapeutically active materials.

We claim:
1. A method for the treatment of hyperlipidemic and antherogenic conditions, said method comprising the step of administering to a mammal in need thereof an effective amount of non-β-oxidizable fatty acid analogues of the formula

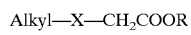

Alkyl—X—CH$_2$COOR wherein the alkyl is a saturated or unsaturated hydrocarbon chain of 8 to 26 carbon atoms, wherein X represents a selenium atom and wherein R represents a hydrogen atom or an alkyl group of 1 to 4 carbon atoms.

2. A method as set forth in claim 1 wherein said alkyl group is a tetradecyl group.

3. A method as set forth in claim 1 wherein said analogue is tetradecylselenoacetic acid.

4. A method for the inhibiting the oxidative modification of low density lipoprotein, said method comprising the step of administering to a mammal an effective amount of non-β-oxidizable fatty acid analogues of the formula

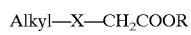

Alkyl—X—CH$_2$COOR wherein the alkyl is a saturated or unsaturated hydrocarbon chain of 8 to 26 carbon atoms, wherein X represents a selenium atom and wherein R represents a hydrogen atom or an alkyl group of 1 to 4 carbon atoms.

5. A method as set forth in claim 4 wherein said alkyl group is a tetradecyl group.

6. A method as set forth in claim 4 wherein said analogue is tetradecylselenoacetic acid.

7. A method for the reduction of the growth of cancer cells, said method comprising the step of administering to a mammal an effective amount of non-β-oxidizable fatty acid analogues of the formula

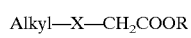

Alkyl—X—CH$_2$COOR wherein the alkyl is a saturated or unsaturated hydrocarbon chain of 8 to 26 carbon atoms, wherein X represents a selenium atom and wherein R represents a hydrogen atom or an alkyl group of 1 to 4 carbon atoms.

8. A method as set forth in claim 1 wherein said alkyl group is a tetradecyl group.

9. A method as set forth in claim 1 wherein said analogue is tetradecylselenoacetic acid.

10. A method for inhibiting the oxidative modification of low density lipo- protein, said method comprising the step of administering to a mammal an effective amount of non-β-oxidizable fatty acid analogues of the formula

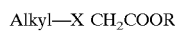

Alkyl—X CH$_2$COOR wherein the alkyl is a saturated or unsaturated hydrocarbon chain of 8 to 26 carbon atoms wherein X represents sulfur and wherein R represents a hydrogen atom or an alkyl group of 1 to 4 carbon atoms.

11. A method as set forth in claim 5 wherein said alkyl group is a tetradecyl group.

12. A method as set forth in claim 5 wherein said analogue is tetradecylthioacetic acid.

13. A method for the reduction of the growth of cancer cells, said method comprising the step of administering to a mammal an effective amount of non-β-oxidizable fatty acid analogues of the formula Alkyl—X CH$_2$COOR wherein the alkyl is a saturated or unsaturated hydrocarbon chain of 8 to 26 carbon atoms wherein X represents sulfur and wherein R represents a hydrogen atom or an alkyl group of 1 to 4 carbon atoms.

14. A method as set forth in claim 13 wherein said alkyl group is a tetradecyl group.

15. A method as set forth in claim 13 wherein said analogue is tetradecylthioacetic acid.

* * * * *